(12) United States Patent
Temple

(10) Patent No.: US 6,336,920 B1
(45) Date of Patent: Jan. 8, 2002

(54) INCONTINENCE DEVICE WITH INTEGRAL APPLICATOR MEANS

(76) Inventor: John E. Temple, 2442 McKinley, Chelsea, MI (US) 48118

( * ) Notice: Subject to any disclaimer, the term of this patent is extended or adjusted under 35 U.S.C. 154(b) by 0 days.

(21) Appl. No.: 09/328,284

(22) Filed: Jun. 8, 1999

(51) Int. Cl.$^7$ .................................................. A61F 5/44
(52) U.S. Cl. ...................................... 604/355; 604/339
(58) Field of Search ............................... 604/332, 355, 604/349, 327, 341, 339, 342

(56) References Cited

U.S. PATENT DOCUMENTS

| | | | |
|---|---|---|---|
| 4,850,986 A | | 7/1989 | Temple ...................... 604/355 |
| 5,593,397 A | * | 1/1997 | La Gro |
| 5,785,695 A | * | 7/1998 | Sato et al. ................... 604/339 |

* cited by examiner

Primary Examiner—Anhtuan T. Nguyen
Assistant Examiner—Michael M. Thompson
(74) Attorney, Agent, or Firm—Gifford, Krass, Groh, Sprinkle, Anderson & Citkowski, PC

(57) ABSTRACT

An incontinence device integrates a fillable bag which, when filled with a gas or liquid, assumes a manually graspable form suitable for use as an applicator. The fillable bag may be adjacent the waste-receiving bag, within the waste-receiving bag, or closure means may be provided enabling the waste-receiving bag itself to function temporarily as the fillable bag. In all embodiments, should the end of the waste-receiving bag include a thermally activated adhesive to improve the integrity of contact to a recipient, the fillable bag may be filled with warm water or other liquid to provide the additional function of causing or at least enhancing the activation of the adhesive. As a further alternative, chemicals may be provided to initiate one or more reactions to generate heat to activate the adhesive and/or to produce a gas to fill the form.

22 Claims, 3 Drawing Sheets

INCONTINENCE DEVICE WITH INTEGRAL APPLICATOR MEANS

FIELD OF THE INVENTION

This invention relates generally to incontinence devices, and, in particular, to a fecal incontinence device wherein a gas- or liquid-fillable bag is used as an applicator.

BACKGROUND OF THE INVENTION

There are many medical and veterinary situations where a biological substance, such as blood, urine, feces, serum, etc. is drained and collected from the body of a patient as the substance is being produced. For example, it is known to attach devices such as colostomy bags and fecal incontinence devices to natural or surgically created orifices of the patient's body for collection of the feces which is produced. See, for example, my U.S. Pat. No. 4,850,986 and patents referenced therein, for a description of a fecal incontinence device.

Typical substance collection bags make it possible for a patient to stay clean and dry even when the patient is comatose or otherwise indisposed. Applying articles of this type may be difficult, however, particularly if the patient is overweight, incapacitated, or both. It often requires two individuals to apply these devices, one to move the patient, and the other to actually install the appliance. Although applicators are available for this purpose, they tend to be separate items which must be dealt with on an independent basis, including disposal. In addition, although modern incontinence devices include an adhesive which is thermally activated, care-giving personnel often do not take sufficient time to activate this adhesive sufficiently, resulting in a failed seal and the need for reapplication. The need remains, therefore, for an integral applicator for use with such devices, and one wherein, ideally, a warm liquid could be used to activate the adhesive, where possible.

SUMMARY OF THE INVENTION

The present invention improves upon existing incontinence devices and like appliances, which currently utilize separate, rigid applicator elements, by providing a fillable bag which, when filled, assumes a manually graspable form suitable for use as an applicator.

With respect to a fecal incontinence device, the invention preferably provides a thin-walled, elongated waste-receiving bag and the same or a separate fillable bag which is temporarily filled with a gas such as air or a liquid or such as water. The resulting structure is sufficiently rigid that a care-giver may grasp the device and urge the opening of the waste-receiving bag against a recipient, after which the bag used as an applicator may be emptied. One advantage of using a gas or liquid as opposed to a solid structure is that the gas or liquid more readily conforms to a particular recipient's anatomy.

The invention contemplates at least three preferred embodiments, wherein the fillable bag is adjacent the waste-receiving bag, within the waste-receiving bag, or wherein closure means are provided enabling the waste-receiving bag itself to function temporarily as the fillable bag. In all embodiments, should the end of the waste-receiving bag include a thermally activated adhesive to improve the integrity of contact to a recipient, the fillable bag may be filled with warm water or other liquid to provide the additional function of activating the adhesive.

According to the embodiment of the invention wherein the fillable bag is adjacent the waste-receiving bag, both bags preferably include capped drainage ports, enabling the fillable bag to be filled and emptied after application, and enabling the waste-receiving bag to be drained periodically once adhered. Although the fillable bag according to this embodiment attaches on one side of the waste-receiving bag, when the waste-receiving bag is deflated and the fillable bag is filled, grasping of the device causes the end of the fillable bag toward the recipient to be urged into intimate contact with the adhesive area, thereby permitting thermal activation.

According to a second embodiment of the invention, the fillable bag is disposed substantially within the waste-receiving bag, in which case the drainage port of the waste-receiving bag is utilized to fill and empty the fillable bag contained therein. Filling of the internal bag may conveniently be carried out with an gas- or liquid-filled syringe, and the fillable bag includes separate closure means to ensure that it remains filled during application of the device.

According to a third embodiment of the invention, the waste-receiving bag and fillable bag are one in the same. To ensure that the contents of the fillable bag are not expelled during application, the recipient-receiving end of the structure is blocked with an internal seal, preferably including a pull string that extends through the bag and out the drainage end. Use of the invention according to this embodiment includes the process of filling the bag with a gas or liquid and having the recipient-receiving end blocked off, and with the pull string extending through the bag and out the drainage end, but captured through the plug at the drainage end. Following application, the drainage end is opened, and the string is pulled, causing the seal to become disengaged and detached from the waste-receiving end, enabling it to be pulled through the drainage port or left in the waste-receiving bag, with the port then recapped for use.

In further alternative embodiments of the invention, chemicals may be provided to initiate one or more reactions to generate heat to activate the adhesive and/or to produce a gas to fill the form. In addition, particularly where the fillable bag is disposed along side the waste-receiving bag, the fillable bag may be provided to the care-giver as a separate component and used on an as-needed basis.

DETAILED DESCRIPTION OF THE INVENTION

Figure 1:
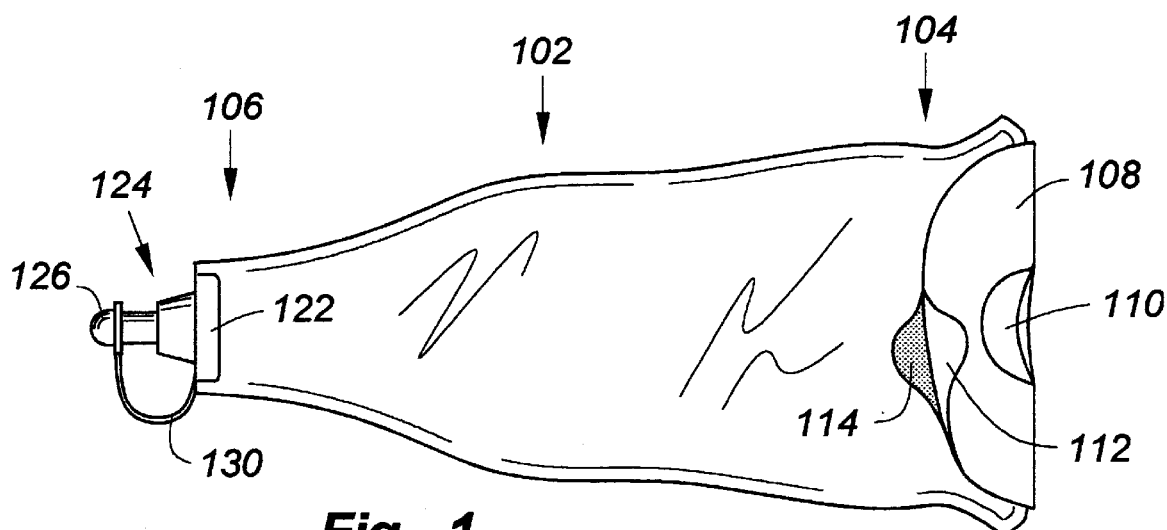
FIG. 1 is a drawing of a prior-art fecal incontinence device.

FIG. 1 is a drawing of a prior-art fecal incontinence device consisting of a waste-receiving bag portion 102 having a recipient-contacting end 104, and a drainage end depicted generally at 106. The recipient-contacting end 104, at least in this example, includes an annular member 108 having a central aperture 110 through which waste is received into the bag 102. The annular member 108 is preferably somewhat stiffened, and includes a base layer 114 having a thermally activated adhesive, and a release layer 112. It should be noted that although the use of an adhesive is preferred, a thermally activated adhesive in particular, the invention is not limited in this regard and may be used with alternative attachment means.

The drainage end 106 of the prior-art device of FIG. 1 includes a drainage port 124 including an apertured portion 122 making a liquid-tight seal to the bag 102. The portion 122 includes a central path therethrough, which communicates to a stem having a cap 126 which is tethered to the body of the device through a connector 130. With the exception of the annular member and its adhesive, the components of the device are constructed of an inexpensive plastic, with the bag 102 being thin-walled and preferably tubular in shape, as shown.

To apply the device of FIG. 1, it is recommended that the care-giver sandwich the member 108 between his or her hands to warm the adhesive, after which a separate applicator is used, as disclosed in my previous U.S. Pat. Nos. 4,850,986 and 5,421,827. One disadvantages of the current approach is the unwillingness on the part of care-giving personnel to hold the annular member long enough to activate the adhesive. The use of a separate applicator is typically more expensive and problematic, in that it must be supplied and/or disposed of separately. The subject invention alleviates the need for separate components through the provision of an integrated applicator while, at the same time, allows the use of warm water to activate an adhesive of this type, if so desired.

Figure 2A:
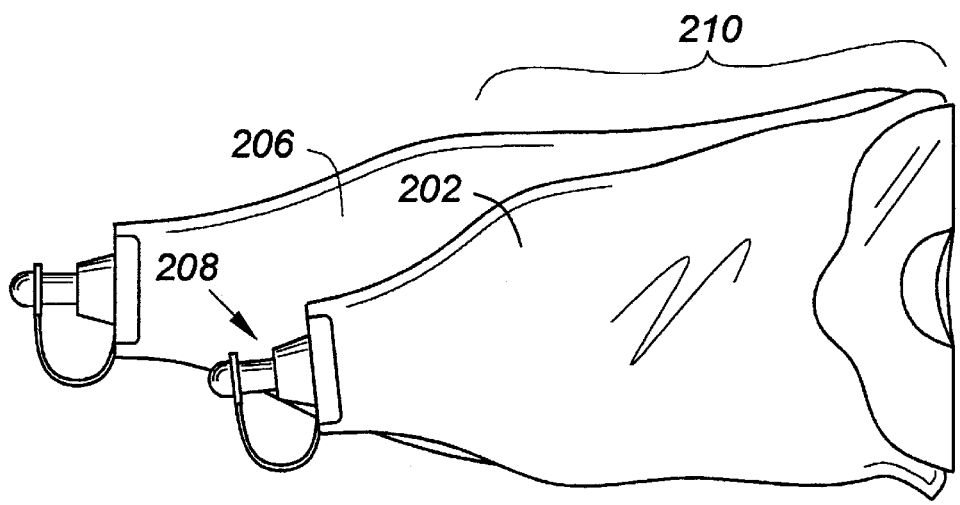
FIG. 2A is a drawing of a first embodiment of the invention, wherein a fillable bag is disposed along side and substantially coextensively with a waste-receiving bag.

FIG. 2A illustrates from one perspective an embodiment of the invention wherein a fillable bag 202 is disposed along side and co-extensively with a waste-receiving bag 206. The bag 202 includes its own port 208 for filling and draining with respect to a procedure also described herein. The bag 202 is preferably immediately adjacent to the bag 206, at least in the region 210, and may either be provided as an entirely separate bag or, depending upon the manufacturing process, the same wall may be shared between bags 202 and 206.

Figure 2B:
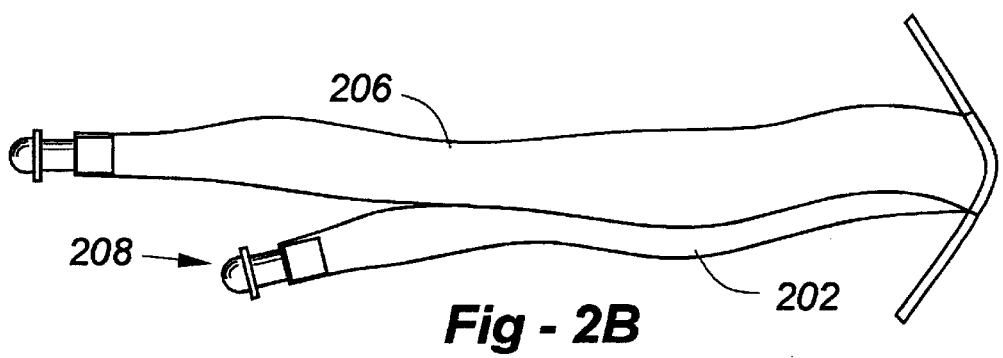
FIG. 2B is a different view of the embodiment of FIG. 2A, illustrating the side-to-side nature of the waste-receiving bag and fillable bag.
Figure 2C:
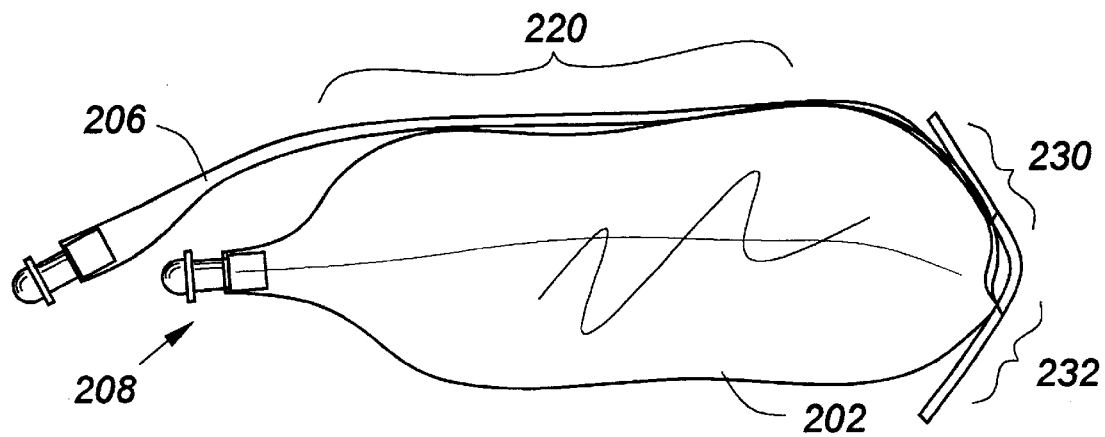
FIG. 2C illustrates the embodiment of FIGS. 2A and 2B, but with the fillable bag having been filled with warm water, and illustrating how, when grasped and urged toward a recipient, the warm liquid makes substantial contact to a thermally activated adhesive.

FIG. 2B is a view of the embodiment of FIG. 2A, as seen from a different perspective, which better illustrates the side-to-side nature of the adjacent bags and 202 and 206. Although the bag 202 must necessarily be disposed along only one side of the bag 206, as shown in FIG. 2C, when filled and urged against a recipient, the forward portions of the bag 202 make sufficient contact with the areas of the annular member in the regions 230 and 232, to activate an adhesive, if so supplied. According to this embodiment, with the waste-receiving 206 deflated as shown, the care-giver would grasp both bags in unison in a vicinity 220, causing the contact regions 230 and 232 to develop as the structure is moved rightwardly in the figure.

Figure 3A:
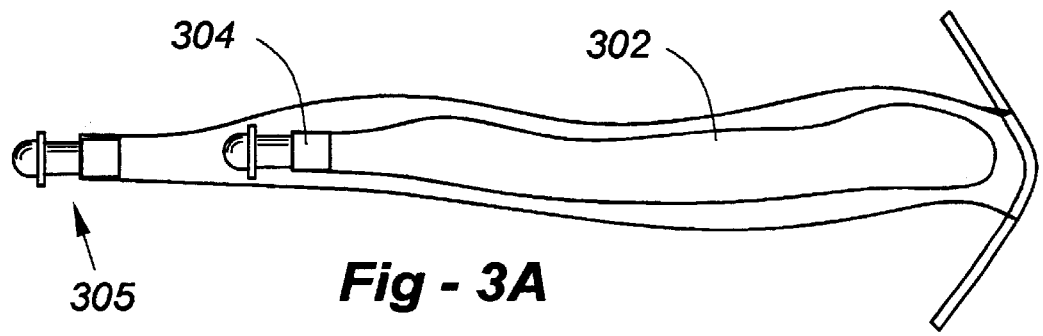
FIG. 3A is a top-view drawing of an alternative embodiment of the invention, wherein a fillable bag used as an applicator is contained within a waste-receiving bag.

FIGS. 3A through 3D illustrate different embodiments of the invention, wherein the fillable bag used for applicator purposes is contained partially or entirely within a waste-receiving bag. In FIG. 3A, an inner bag 302 would be filled through ports 304 and 305 using a syringe with a sufficiently long end to extend through both ports when both ports are open. Due to the flexible nature of the waste-receiving bag 303, it is not difficult to open and close the port 304 through the wall of the bag 303, even though the port 304 and bag 302 are contained entirely within the bag 303.

Figure 3B:
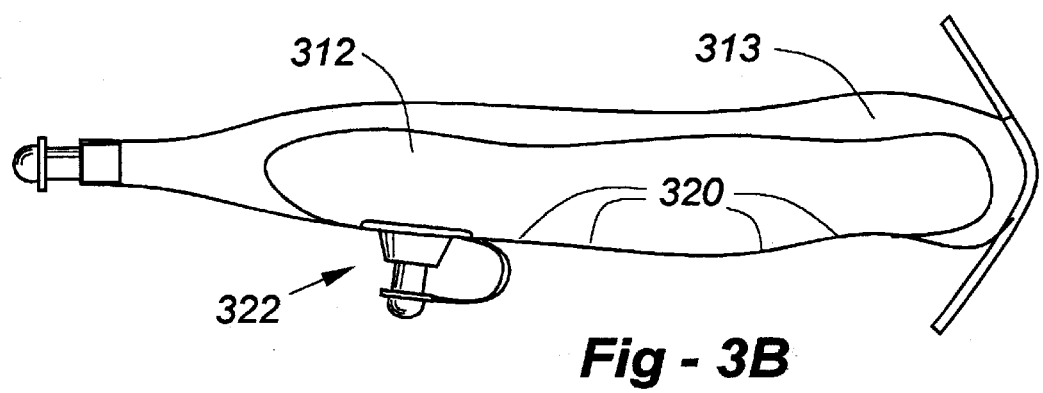
FIG. 3B is related to FIG. 3A, except that a common wall is used between the waste-receiving and fillable bags.
Figure 3C:
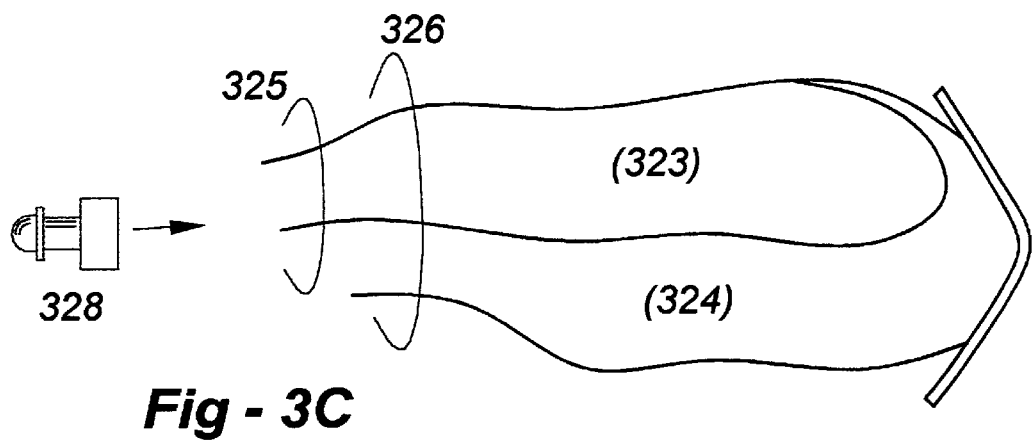
FIG. 3C shows a different bag-within-a-bag structure, wherein a fillable bag is contained within a waste-receiving bag having an open drainage end.
Figure 3D:
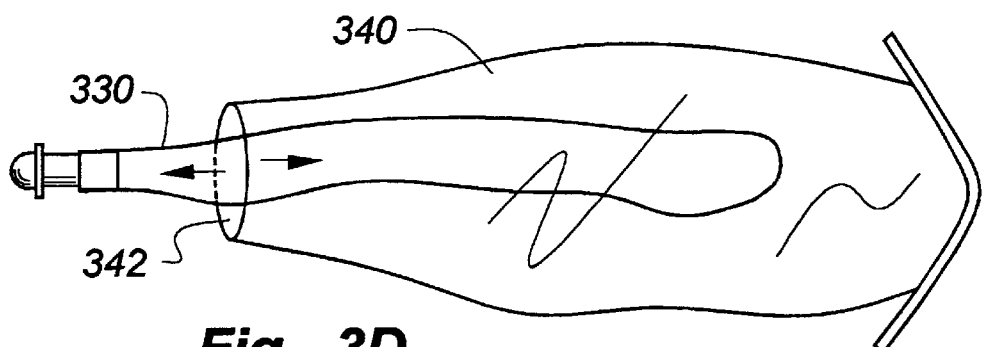
FIG. 3D shows an alternative embodiment wherein a fillable bag may be inserted into, and removed from, a bag of the type having an open drainage end.

In FIG. 3B, a fillable bag 312 and a waste-receiving bag 313 share a common wall 320, which may contain one or more plies depending upon manufacturing considerations. A port 322, provided for filling and emptying, may conveniently take the form of a "soft port" of the type used on beach equipment, or more elaborate seals may be used. FIG. 3C is an alternative structure wherein a fillable bag 323 consumes a portion of the volume within a waste-receiving bag 324, and wherein a clamp, clip or other such device is used to seal the bag 323 at 325, and a clamp, clip or other such device is used to seal the waste-receiving or both bags at 326. In place of a clamp or clip, one or more ports 328 may alternatively be provided. FIG. 3D shows a different bag-within-a-bag structure, wherein a fillable bag 330 is contained within a waste-receiving bag 340 having an open drainage end 342 of the type utilizing a solid-form applicator, as described in my issued U.S. Pat. Nos. 4,850, 986 and 5,421,847.

Figure 4:
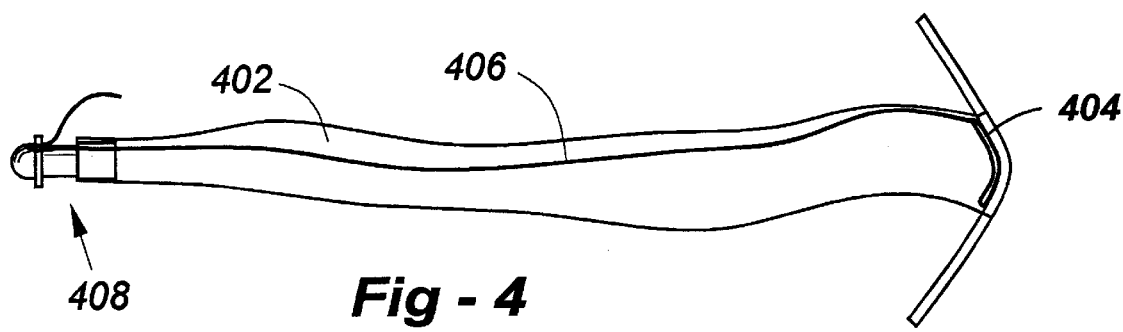
FIG. 4 is yet a further alternative embodiment of the invention, wherein the waste-receiving bag functions itself as a fillable bag which is emptied following application.

FIG. 4 illustrates yet a further alternative embodiment according to the invention, wherein the waste-receiving bag 402 and the fillable bag are one in the same. According to this embodiment, it is necessary to seal off the opening at the recipient-contacting end, and this is preferably carried out through a seal 404 connected to a string 406. For use as an applicator, the tab at the drainage end of the structure is removed, and the bag 402 is filled with air or, more preferably, a warm liquid such as water, in the event that a thermally activated adhesive is used. The port 408 is then capped off, though the string 410 remains externally available, as shown. The resiliency of the various materials, and the cross-section and geometry of the string 410 may be adjusted so that when the bag 402 is filled and the cap replaced at the end 408, the end at 408 will not leak even with the string 410 externally exposed.

Following application, the cap on port 408 is removed, and the string 410 is pulled, causing the seal 404 to lift off of the opening at the recipient-contacting end, and again, by adjusting the flexibility and dimensions of the various components, the string and seal 404 may either be pulled entirely through the port 408, or left in the waste-receiving bag 402 having opened u p the recipient-contacting opening and, perhaps, with excess string 410 being clipped off.

Figure 5:
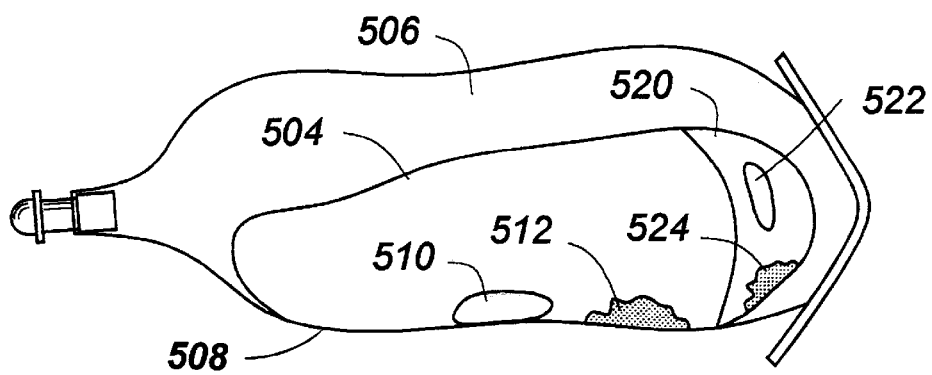
FIG. 5 is a drawing which shows how chemicals in sealed containers may be released to generate heat and/or a gas for filling the applicator bag.

FIG. 5 is a drawing which shows how chemical reactions may be used to generate a gas to induce rigidity and/or generate heat to activate an adhesive, or both functions may be provided, as shown. In terms of gas production, a fillable bag 504, in this case contained within a waste-receiving bag 506 and sharing a common wall 508, includes a first material 510 and a second material 512 which, when allowed to react, generate a gas to fill the bag 504. For example, the material 510 may be vinegar contained in an ampule as shown, and the material 512 may be baking soda, the combination being used to generate carbon dioxide and induce rigidity when the ampule 510 is broken through external pressure.

In terms of heat generation, a separate compartment 520 is preferably provided, wherein materials 522 and 524 react to create heat. A separate compartment 520 is preferably utilized to concentrate the heat production near the adhesive end of the structure. In terms of heat-producing materials, any combination may be used, such as fine calcium chloride crystals (524) and water, which would be contained in the ampule designated by numerical reference 522. Use of a common wall 508 enables the gas generated through the reaction of materials 510 and 512 to escape through a small puncture or, alternatively, a port may be provided for such purpose.

It should be noted that, although FIG. 5 shows both gas- and heat-producing chemical combinations, these reactions may be provided separately, or in combination, as desired. In addition, although a bag-within-a-bag structure is shown in FIG. 5, the chemicals used to produce a gas and/or heat may be used in conjunction with any of the embodiments previously described and, indeed, the heat-producing reaction may be used independently of a fillable bag structure. That is, the heat-producing reaction may be provided in conjunction with more conventional incontinence devices wherein solid applicators are used, with the heat-producing materials being used to at least enhance the activation of the adhesive, where so provided. For that matter, the use of a warm liquid such as water or the heat-producing materials as described herein may be provided in conjunction with other types of adhesive-bearing appliances, such as colostomy and illeostomy devices.

I claim:

1. An incontinence device, comprising:
    a waste-receiving bag having a recipient-contacting end and a drainage end;
    the recipient-contacting end of the waste-receiving bag including an aperture through which waste material is received and an adhesive-bearing member surrounding the aperture; and
    a fillable bag which is at least temporarily sealable, such that when sealed and filled, the fillable bag assumes a manually graspable form enabling the recipient-contacting end to be urged against a recipient without loss of the filler.

2. The device of claim 1, wherein the fillable bag is filled with a liquid to assume the manually graspable form.

3. The device of claim 2, wherein:
    at least a portion of the adhesive is thermally activated; and
    the fillable bag is filled with warm water to at least enhance the activation of the adhesive.

4. The device of claim 1, wherein:
    at least a portion of the adhesive is thermally activated; and
    the device includes one or more chemicals which generate heat to at least enhance the activation of the adhesive.

5. The device of claim 1, wherein the fillable bag is filled with a gas to assume the manually graspable form.

6. The device of claim 5, wherein the gas is air.

7. The device of claim 5, further including one or more chemicals to generate the gas.

8. The device of claim 1, wherein the fillable bag is disposed adjacent and alongside at least a portion of the waste-receiving bag in a co-extensive manner.

9. The device of claim 1, wherein the fillable bag is disposed substantially within the waste-receiving bag.

10. The device of claim 1, further including a removable seal disposed over the aperture enabling the waste-receiving bag to function as the fillable bag.

11. The device of claim 10, further including:
    an elongated pull element accessible through the drainage end enabling the seal to be removed from the aperture after the device is in place.

12. An incontinence device, comprising:
    a waste-receiving bag having a recipient-contacting end and a drainage end;
    the recipient-contacting end including an aperture through which waste material is received and an annular member with a thermally activated adhesive surrounding at least a portion of the aperture; and
    fillable bag integral to the device which, when filled, may be grasped without loss of the filler and used to apply the device to a recipient.

13. The device of claim 12, wherein the fillable bag is at least temporarily sealable and disposed adjacent and alongside at least a portion of the waste-receiving bag in a co-extensive manner.

14. The device of claim 12, wherein the fillable bag is at least temporarily sealable and disposed substantially within the waste-receiving bag.

15. The device of claim 12, further including a removable seal disposed over the aperture enabling the waste-receiving bag and the fillable bag are one and the same.

16. The device of claim 15, further including:
    an elongated pull element accessible through the drainage end, enabling the seal to be removed from the aperture after the device is in place.

17. The device of claim 12, wherein the fillable bag is filled with a liquid.

18. The device of claim 17, wherein the liquid is a warm liquid and used at least to enhance the activation of the adhesive.

19. The device of claim 12, further including one or more chemicals which generate heat to activate the adhesive.

20. The device of claim 12, wherein the fillable bag is filled with a gas.

21. The device of claim 20, wherein the gas is air.

22. The device of claim 12, further including one or more chemicals to generate the gas.

* * * * *

UNITED STATES PATENT AND TRADEMARK OFFICE
CERTIFICATE OF CORRECTION

PATENT NO.    : 6,336,920 B1                                              Page 1 of 1
DATED         : January 8, 2002
INVENTOR(S)   : John E. Temple It is certified that error appears in the above-identified patent and that said Letters Patent is hereby corrected as shown below:

<u>Title page,</u>
Item [56], References Cited, La Gro references classes are 604/355

<u>Column 4,</u>
Line 58, replace "u p" with -- up --.

<u>Column 6,</u>
Line 27, before "fillable bag" insert -- a --.

Signed and Sealed this

Seventeenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,336,920 B1
DATED : January 8, 2002
INVENTOR(S) : John E. Temple

It is certified that error appears in the above-identified patent and that said Letters Patent is hereby corrected as shown below:

Title page,
Item [56], References Cited, La Gro references classes are 604/355

Column 4,
Line 58, replace "u p" with -- up --.

Column 6,
Line 27, before "fillable bag" insert -- a --.

Signed and Sealed this

Fifteenth Day of October, 2002

*Attest:*

*Attesting Officer*

JAMES E. ROGAN
*Director of the United States Patent and Trademark Office*